(12) United States Patent
Paine et al.

(10) Patent No.: US 12,036,669 B2
(45) Date of Patent: Jul. 16, 2024

(54) EXOSKELETON DEVICE WITH IMPROVED ACTUATION SYSTEM

(71) Applicant: Apptronik, Inc., Austin, TX (US)

(72) Inventors: Nicholas Arden Paine, Austin, TX (US); Jonas Fox, Austin, TX (US)

(73) Assignee: Apptronik, Inc., Austin, TX (US)

( * ) Notice: Subject to any disclaimer, the term of this patent is extended or adjusted under 35 U.S.C. 154(b) by 982 days.

(21) Appl. No.: 16/979,057

(22) PCT Filed: Mar. 8, 2019

(86) PCT No.: PCT/US2019/021413
§ 371 (c)(1),
(2) Date: Sep. 8, 2020

(87) PCT Pub. No.: WO2019/173751
PCT Pub. Date: Sep. 12, 2019

(65) Prior Publication Data
US 2021/0053208 A1 Feb. 25, 2021

Related U.S. Application Data

(60) Provisional application No. 62/640,075, filed on Mar. 8, 2018.

(51) Int. Cl.
*B25J 9/00* (2006.01)
*A61H 3/00* (2006.01)

(52) U.S. Cl.
CPC .............. *B25J 9/0006* (2013.01); *A61H 3/00* (2013.01); *A61H 2201/1215* (2013.01);
(Continued)

(58) Field of Classification Search
CPC .. B25J 9/0006; A61H 3/00; A61H 2201/1215; A61H 2201/123;
(Continued)

(56) References Cited

U.S. PATENT DOCUMENTS 5,904,721 A * 5/1999 Henry .................... A61F 2/644
623/44
8,870,967 B2 10/2014 Herr et al.
(Continued)

FOREIGN PATENT DOCUMENTS

WO WO2015099858 7/2015
WO WO2019076417 A1 4/2019

OTHER PUBLICATIONS

Army-Technology.com [online], "Raytheon XOS 2 Exoskeleton, Second-Generation Robotics Suit," May 29, 2020, retrieved on Sep. 8, 2022, retrieved from URL <https://www.army-technology.com/projects/raytheon-xos-2-exoskeleton-us/>, 9 pages.
(Continued)

*Primary Examiner* — Ariana Zimbouski
*Assistant Examiner* — Christine L Nelson
(74) *Attorney, Agent, or Firm* — Fish & Richardson P.C.

(57) ABSTRACT

An exoskeleton device in accordance with the present disclosure may generally include a series elastic actuator (SEA), a slider-crank mechanism and a four bar linkage mechanism. The SEA includes a motor and a ball screw coupled to a shaft of the motor via a shaft coupler, which transfers rotational motion of the shaft directly to the ball screw. The slider-crank mechanism includes a ball nut and a crank. As the ball screw rotates, the ball nut converts rotational motion of the ball screw into linear motion of the ball nut to drive the crank. The crank converts linear motion of the ball nut back into rotational motion at the input of the four bar linkage mechanism. The four bar linkage mechanism is coupled to an output of the crank and configured to provide a complex motion profile that emulates kinematics of a wearer's joint.

26 Claims, 11 Drawing Sheets

(52) U.S. Cl.
 CPC ............... *A61H 2201/123* (2013.01); *A61H 2201/1436* (2013.01); *A61H 2201/1628* (2013.01); *A61H 2201/1642* (2013.01); *A61H 2201/165* (2013.01); *A61H 2201/5058* (2013.01); *A61H 2205/088* (2013.01); *A61H 2205/102* (2013.01)

(58) Field of Classification Search
 CPC .... A61H 2201/1436; A61H 2201/1628; A61H 2201/1642; A61H 2201/165; A61H 2201/5058; A61H 2205/088; A61H 2205/102
 See application file for complete search history.

(56) References Cited

U.S. PATENT DOCUMENTS

| | | | |
|---|---|---|---|
| 11,035,743 | B2 | 6/2021 | Paine et al. |
| 2011/0040216 | A1 | 2/2011 | Herr et al. |
| 2012/0283845 | A1 | 11/2012 | Herr et al. |
| 2013/0310979 | A1 | 11/2013 | Herr et al. |
| 2015/0209214 | A1* | 7/2015 | Herr ............... A61H 1/0266 623/27 |
| 2016/0113831 | A1 | 4/2016 | Hollander |
| 2016/0250094 | A1 | 9/2016 | Amundson et al. |
| 2017/0341227 | A1 | 11/2017 | Sentis et al. |
| 2018/0065243 | A1 | 3/2018 | Kim et al. |
| 2018/0116828 | A1* | 5/2018 | Quinn ............... B25J 9/0006 |
| 2021/0298922 | A1* | 9/2021 | Sun ............... A61F 2/64 |

OTHER PUBLICATIONS

Eksobionics.com [online], "EksoGT," available on or before Jul. 13, 2017, via Internet Archive: Wayback Machine URL <http://web.archive.org/web/20170713095157/https://eksobionics.com/eksohealth/products/>, retrieved on Sep. 8, 2022, URL <https://eksobionics.com/eksohealth/products/>, 10 pages.

Paine et al., "Actuator Control for the NASA-JSC Valkyrie Humanoid Robot: A Decoupled Dynamics Approach for Torque Control of Series Elastic Robots," Journal of Field Robotics, May 2015, 32(3):378-396.

Robots.ihmc.us [online], "NASA-IHMC X1 Mina Exoskeleton," available on or before Jan. 25, 2018, via Internet Archive: Wayback Machine URL <http://web.archive.org/web/20180125004907/http://robots.ihmc.us/x1-mina-exoskeleton/>, retrieved on Sep. 8, 2022, URL <http://robots.ihmc.us/x1-mina-exoskeleton/>, 5 pages.

Robots.ihmc.us [online], "The Grasshopper Exercise Device," available on or before Jul. 17, 2017, retrieved on Sep. 8, 2022, retrieved from URL <http://robots.ihmc.us/grasshopper/>, 7 pages.

Sarcos.com [onlline], "Guardian® XO® Full-Body Powered Exoskeleton," available on or before Mar. 1, 2020, via Internet Archive: Wayback Machine URL <http://web.archive.org/web/20200301031510/https://www.sarcos.com/products/guardian-xo-powered-exoskeleton/>, retrieved on Sep. 8, 2022, URL <https://www.sarcos.com/products/guardian-xo-powered-exoskeleton/>, 9 pages.

International Search Report and Written Opinion issued for International PCT Application No. PCT/US19/21413, mailed on May 29, 2019, 6 pages.

Chen et al., "Mechanical Design and Evaluation of a Compact Portable Knee-Foot Robot for Gait Rehabilitation," Elsevier, Mechanism and Machine Theory 103 (2016) pp. 51-64.

Ansari et al., "A Survey of Current Exoskeletons and Their Control Architectures and Algorithms (Draft 4.0)," Carnegie Mellon University, Oct. 1, 2015, 42 pages.

Kim, "Anthropomorphic Low-Inertia High-Stiffness Manipulator for High-Speed Safe Interaction," IEEE Transactions on Robotics, Dec. 2017, 33(6):1358-1374.

* cited by examiner

EXOSKELETON DEVICE WITH IMPROVED ACTUATION SYSTEM

PRIORITY CLAIM

This is a national stage application of and claims the benefit of priority to International Application No. PCT/US2019/021413 filed Mar. 8, 2019, entitled "EXOSKELETON DEVICE WITH IMPROVED ACTUATION SYSTEM," which claims priority to U.S. Provisional Application No. 62/640,075, filed on Mar. 8, 2018, entitled "EXOSKELETON DEVICE WITH IMPROVED ACTUATION SYSTEM," the entire contents of which are hereby expressly incorporated by reference for all purposes.

STATEMENT REGARDING FEDERALLY SPONSORED RESEARCH OR DEVELOPMENT

This invention was made with government support under Contract Numbers H92222-17-C-0050 and H92222-17-C-0074 awarded by the Department of Defense designated Headquarters U.S. Special Operations Command (USSOCOM). The government has certain rights in the invention.

FIELD

This invention relates generally to exoskeleton devices, and more particularly, to exoskeleton devices having improved actuation systems.

BACKGROUND

Exoskeleton devices have been developed for prosthetic, orthotic and human strength assistive use, and have been used to emulate the kinematics of human joints, amplify the strength of the wearer by applying assistive torques to the wearer's joints, and support the weight of the wearer and/or a payload carried by the wearer. These exoskeleton devices typically include a rigid framework having one or more articulated joints (e.g., a knee joint and ankle joint in a lower extremity exoskeleton device), and one or more actuators for controlling joint articulation.

The actuators used within exoskeleton devices are ideally compact and lightweight, yet able to generate high power and force with high efficiency. Actuators that are overly bulky or heavy limit the performance of the exoskeleton device, and often cannot be used in dense high-degree-of-freedom exoskeleton designs. In addition, actuators used in exoskeleton devices are preferably robust, impact tolerant and capable of providing precise position and force control. While some actuator designs may provide a subset of the desired attributes (e.g., power density, efficiency, impact tolerance, position controllability and force controllability), most actuator designs fail to provide all of the desired attributes. For example, hydraulic actuators exhibit above average power density, impact tolerance, position controllability and force controllability, but suffer from poor efficiency. Pneumatic actuators exhibit relatively good impact tolerance, but below average performance in other areas. Geared electric (air-cooled) actuators exhibit good efficiency and position controllability, but poor power density, impact tolerance and force controllability.

Exoskeleton devices have recently been designed to include various types of series elastic actuators. A series elastic actuator (SEA) generally contains a motor to generate mechanical power, a transmission mechanism to transfer mechanical power to an output joint, a speed reduction mechanism to amplify motor torque and an elastic element, which is coupled in series with the motor, to detect actuator force applied to a load. The force detected by the SEA can be used to control actuator force and position with a high degree of precision by incorporating the detected force into a feedback control scheme. Compared to other types of actuators, SEAs provide improved power density, efficiency, impact tolerance, position controllability and force controllability. However, most SEA designs remain rather heavy, bulky and/or exhibit other performance limitations that limit their applicability and performance in dense high-degree-of-freedom exoskeleton designs.

SUMMARY OF THE INVENTION

The following description of various embodiments of exoskeleton devices and lower extremity robotic exoskeletons is not to be construed in any way as limiting the subject matter of the appended claims.

According to one embodiment, an exoskeleton device in accordance with the present disclosure may generally include a series elastic actuator (SEA), a slider-crank mechanism and a four bar linkage mechanism. The SEA may generally include a motor and a ball screw, which is coupled to a shaft of the motor via a shaft coupler that transfers rotational motion of the shaft directly to the ball screw. In some embodiments, the SEA may further include two pairs of springs (four springs in total) and an actuator housing. Each pair of springs may be positioned alongside a different side of the motor. In some embodiments, the motor and a lower spring in each pair of springs may be coupled to the actuator housing.

The slider-crank mechanism may generally include a ball nut and a crank. The ball nut is coupled to an upper end of the crank. A lower end of the crank is coupled to an input of the four bar linkage mechanism. As the ball screw rotates, the ball nut converts rotational motion of the ball screw into linear motion of the ball nut to drive the crank. The crank converts the linear motion of the ball nut back into rotational motion at the input of the four bar linkage mechanism. The four bar linkage mechanism is coupled to the output of the crank and configured to provide a complex motion profile that emulates kinematics of a wearer's joint.

In some embodiments, the exoskeleton device may further include a first linear guide mechanism, which is attached to a structural element of the exoskeleton device to provide structural support to, and allow linear motion of, the SEA. The first linear guide mechanism may include a rail portion and a guide portion, which is coupled to and configured to slide along the rail portion. The rail portion may be attached to the structural element of the exoskeleton device and the guide portion may be attached to a lower surface of the actuator housing.

In some embodiments, the exoskeleton device may further include a second linear guide mechanism, which is attached to the structural element of the exoskeleton device to provide structural support to, and allow linear motion of, the ball nut and crank. The second linear guide mechanism may include a rail portion and a guide portion, which is coupled to and configured to slide along the rail portion. The rail portion may be attached to the structural element of the exoskeleton device and the guide portion may be attached to the upper end of the crank.

In some embodiments, the four bar linkage mechanism may include a first link, a second link, a third link and a fourth link. The first link is a T-shaped link having a first end rotationally coupled to the upper end of the crank, a second end rotationally coupled to the second link, and a third end rotationally coupled to the third link. In some embodiments, the second link may be the structural element of the exoskeleton device to which the first linear guide mechanism and the second linear guide mechanism are attached. The third link extends in a dorsal direction to rotationally couple with the fourth link, which is positioned on one side of the wearer's joint.

In some embodiments, the four bar linkage mechanism may be one of a pair of four bar linkage mechanisms included within the exoskeleton device. In such embodiments, each four bar linkage mechanism may include a first link, a second link, and a fourth link, as described above, and the third link may be shared by the pair of four bar linkage mechanisms. The shared third link extends in a lateral direction across the wearer's knee joint to rotationally couple with the third ends of the T-shaped first links included within the pair of four bar linkage mechanisms.

According to another embodiment, a lower extremity robotic exoskeleton in accordance with the present disclosure may generally include an upper subassembly for applying assistive torques to a wearer's knee joint, and a lower subassembly for applying assistive torques to the wearer's ankle joint. The upper subassembly may include a first series elastic actuator (SEA), a first slider-crank mechanism, a pair of four-bar linkage mechanisms and control circuitry, which uses a force detected by the first SEA to control rotation at the wearer's knee joint. The lower subassembly may include a second series elastic actuator (SEA), a second slider-crank mechanism and control circuitry, which uses a force detected by the second SEA to control rotation at the wearer's ankle joint.

In some embodiments, the first SEA and the second SEA may each include a motor, a ball screw coupled to a shaft of the motor, an actuator housing, two pairs of springs, and a spring deflection sensor. Within the first/second SEAs, each pair of springs may be positioned along a different side the motor, and a lower spring in each pair of springs may be coupled to the actuator housing. The spring deflection sensor may be arranged within the actuator housing for detecting the force exerted by the SEA as the springs compress and expand.

In some embodiments, the first slider-crank mechanism and the second slider-crank mechanism may each include a ball nut and a crank. The ball nut may be configured to convert rotational motion of the ball screw into linear motion of the ball nut to drive the crank.

The pair of four-bar linkage mechanisms included within the upper subassembly may be coupled to an output of the crank included in the first slider-crank mechanism, and may be configured to provide a complex motion profile that emulates kinematics of a wearer's joint. Each four bar linkage mechanism may include a first link, a second link, and a fourth link, and a third link may be shared between the pair of four bar linkage mechanisms. The first link included within each four bar linkage mechanism may be a T-shaped link having a first end rotationally coupled to the upper end of the crank, a second end rotationally coupled to the second link, and a third end rotationally coupled to the shared third link. The shared third link may extend in a dorsal direction to rotationally couple with the fourth link, which is positioned on one side of the wearer's knee joint. The shared third link may further extend in a lateral direction across the wearer's knee joint to rotationally couple with the third ends of the T-shaped first links included within the pair of four bar linkage mechanisms.

In some embodiments, the upper subassembly and the lower subassembly may each further include a plurality of structural elements that provide structural support for the exoskeleton. In some embodiments, the plurality of structural elements may include a first structural element, a second structural element, a third structural element and a fourth set of structural elements. The first structural element may extend longitudinally along an outside of the wearer's leg, and the second structural element and the third structural element may arch laterally across the wearer's leg. Lower portions of the second and third structural elements may be fixedly attached to the first structural element. The fourth set of structural elements may be coupled between the second and third structural elements, and may be configured to support the first/second SEA and the first/second slider-crank mechanism.

In some embodiments, the upper subassembly and the lower subassembly may each further include a first linear guide mechanism and a second linear guide mechanism. The first linear guide mechanism may be coupled between the fourth set of structural elements of the exoskeleton device and the actuator housing. The second linear guide mechanism may be coupled between the fourth set of structural elements and an upper end of the crank. The first linear guide mechanism enables the actuator housing of the first/second SEA to slide up and down the fourth set of structural elements with compression and expansion of the springs. The second linear guide mechanism enables the ball nut and crank to slide in a linear motion as the ball screw rotates.

In some embodiments, the upper subassembly and the lower subassembly described above may be fitted to one of the wearer's legs. In other embodiments, the lower extremity robotic exoskeleton may further include a second upper subassembly and a second lower subassembly, which are fitted to another one of the wearer's legs. In such embodiments, the second upper subassembly may be identical to the upper subassembly, and the second lower subassembly may be identical to the lower subassembly.

In some embodiments, the lower extremity robotic exoskeleton may include additional components, which are coupled to the upper subassembly and the second upper subassembly. For example, a pair of hip joint assemblies coupled to the upper subassembly and the second upper subassembly may be positioned on either side of the wearer's hips. The pair of hip joint assemblies may be generally configured to control flexion/extension of the wearer's hip joint. In addition, the lower extremity robotic exoskeleton may include a curved hollow structure coupled to the pair of hip joint assemblies, and a rotary actuator that is coupled to the curved hollow structure to provide abduction/adduction actuation for the wearer's hip joint. In some embodiments, a power unit may be coupled to the rotary actuator to provide power to the rotary actuator, as well as to the SEAs and the control circuitry included within the upper subassembly, the lower subassembly, the second upper subassembly and the second lower subassembly.

BRIEF DESCRIPTION OF THE DRAWINGS

Other advantages of the present disclosure will become apparent upon reading the following detailed description and upon reference to the accompanying drawings in which.

Figure 1:
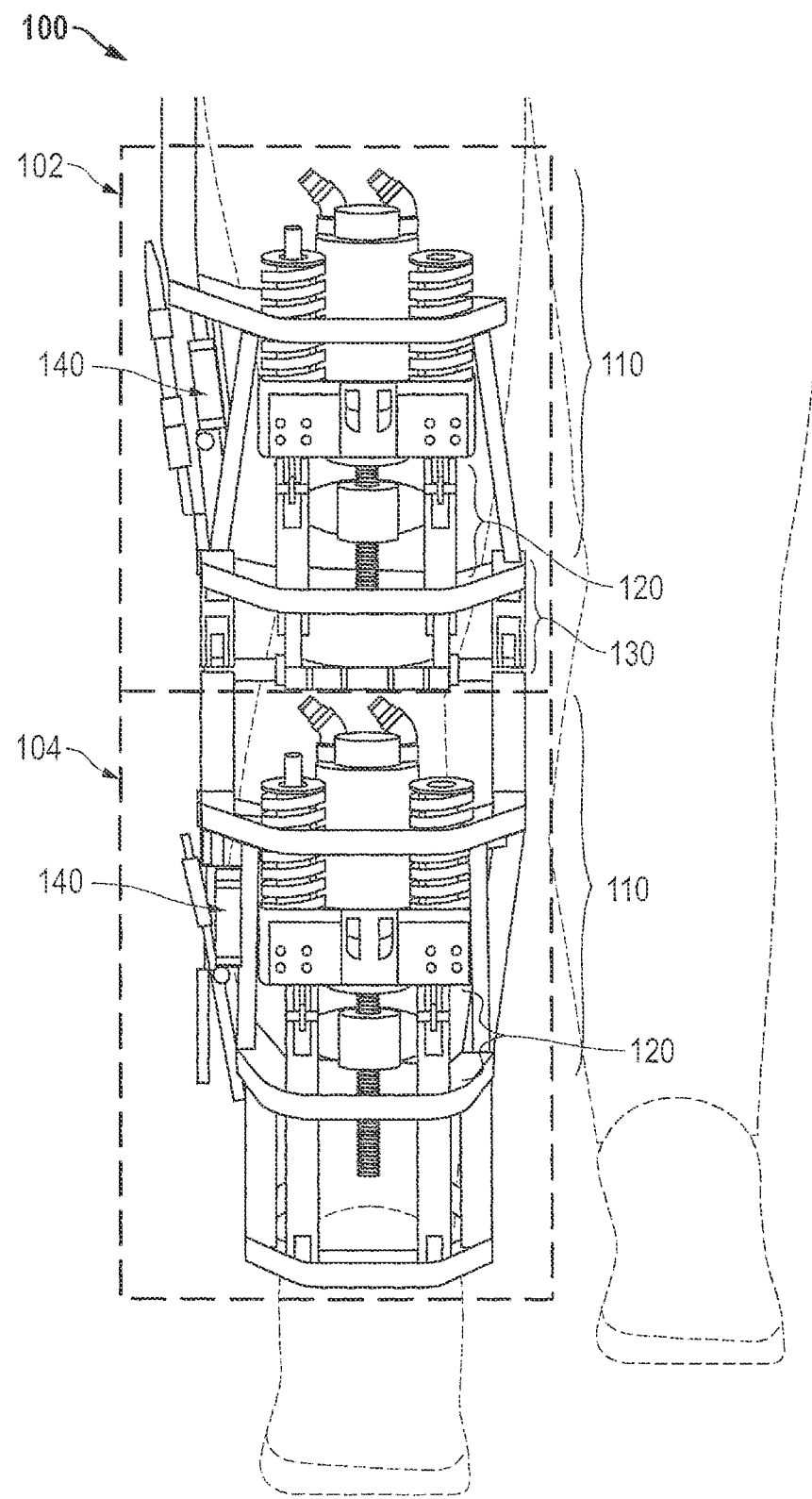
FIG. 1 is a front view of an upper subassembly and a lower subassembly of a lower extremity exoskeleton device, according to one embodiment of the present disclosure.

While the present disclosure is susceptible to various modifications and alternative forms, specific embodiments thereof are shown by way of example in the drawings and will herein be described in detail. It should be understood, however, that the drawings and detailed description thereto are not intended to limit the disclosure to the particular form disclosed, but on the contrary, the present disclosure is to cover all modifications, equivalents and alternatives falling within the spirit and scope of the present disclosure as defined by the appended claims.

DESCRIPTION OF ILLUSTRATIVE EMBODIMENTS

Turning now to the drawings, FIGS. 1-6 illustrate an exoskeleton device 100 with an improved actuation system, according to one embodiment of the present disclosure. Although depicted as a lower extremity exoskeleton device, the inventive concepts set forth herein are not strictly limited to a lower extremity exoskeleton device and may be applied to other exoskeleton devices, which may be configured to support and provide assistive force to other limbs and joints of a wearer.

Figure 2:
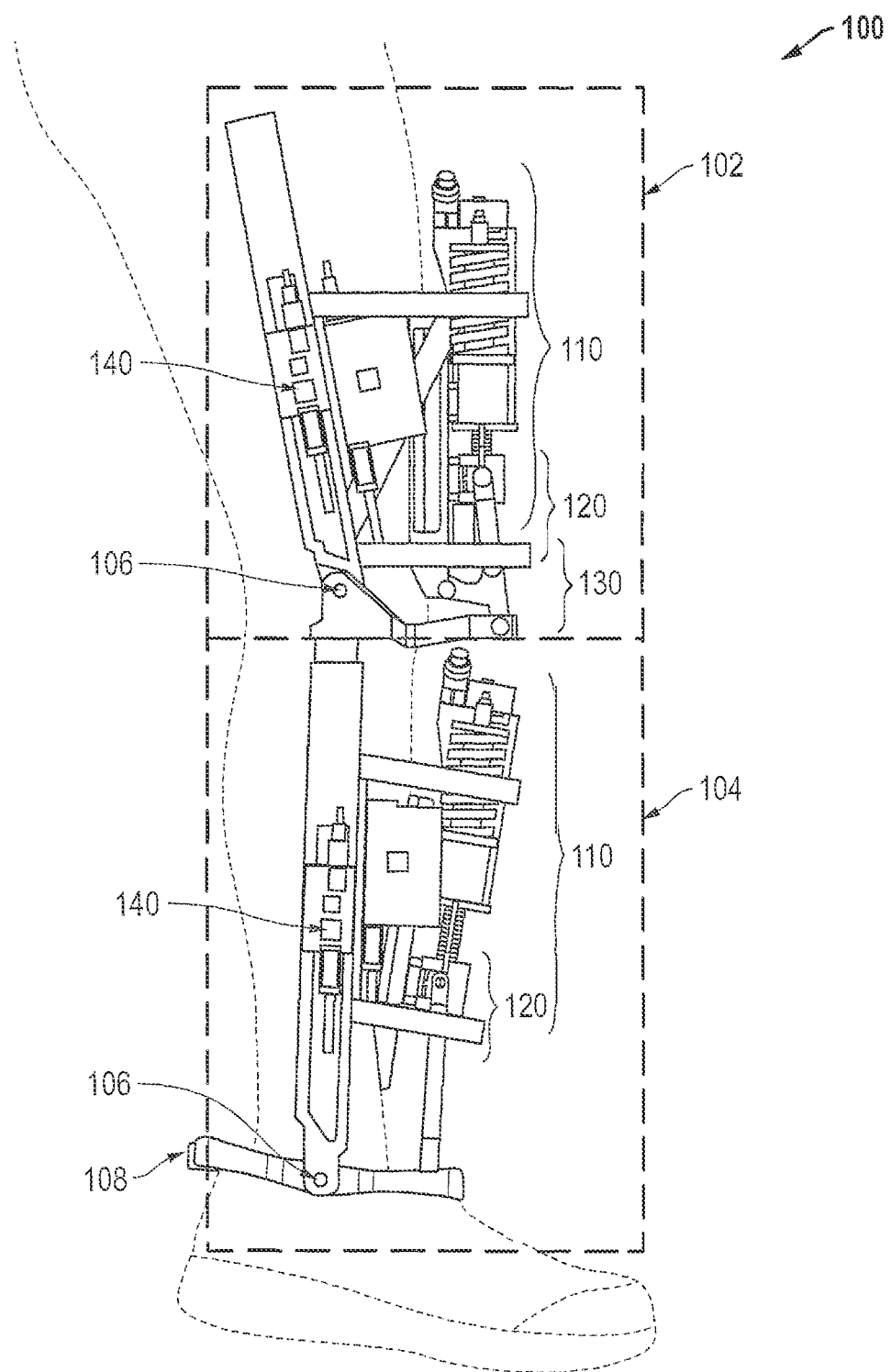
FIG. 2 is a side view of the exoskeleton device shown in FIG. 1.

The exoskeleton device 100 shown in FIGS. 1-6 is a lower extremity exoskeleton device, which provides a load path to ground in parallel to the wearer's leg and is configured to apply a known amount of force to the knee and ankle joints in the Sagittal plane (i.e., the longitudinal plane parallel to the human body dividing the body into left and right sides). As shown in FIGS. 1 and 2, exoskeleton device 100 is composed of two actuated subassemblies, i.e., an upper subassembly 102 for the knee joint and a lower subassembly 104 for the ankle joint. Upper subassembly 102 and lower subassembly 104 each have an active (actuated) degree-of-freedom (DOF) 106 at the joint in the Sagittal plane (see, FIG. 2). In addition to an active DOF 106, lower subassembly 104 has a passive (un-powered) DOF 108 at the ankle joint in the Coronal plane (i.e., the vertical plane dividing the human body into front and back sides) (see, FIG. 2).

As described in more detail below, the active DOF 106 in the knee and ankle joints are actuated by an improved actuation system including a unique series elastic actuator (SEA) design, which positions an elastic element in series with the load path of the actuator for shock absorption and force-sensing purposes. A ball screw is utilized in the unique SEA design as a high-efficiency force amplification mechanism, and linear motion produced by the ball screw is converted into rotational motion by a novel mechanism consisting of a slider-crank and four-bar linkage mechanism. In some embodiments, heat generated by the SEA motor is convectively cooled by fluid, increasing torque density of the device by a factor of 3.6× over an air-cooled actuator of similar design. Other advantages and distinctions of the novel SEA and exoskeleton design will become apparent from the description below.

FIGS. 1-5 provide various views of the upper subassembly 102 of the exoskeleton device 100 depicting various components used to control rotation at the knee joint of the exoskeleton device. As set forth in more detail below, the components used to control rotation at the knee joint may generally include SEA 110, slider-crank mechanism 120, a pair of four-bar linkage mechanisms 130, and control circuitry 140, which uses the force detected by the SEA to control rotation at the knee joint. As shown in FIGS. 1 and 2, lower subassembly 104 also includes a SEA 110, slider-crank mechanism 120 and control circuitry 140 to control rotation at the ankle joint. However, since the ankle requires less range of motion than the knee, the four-bar linkage mechanism 130 used in upper subassembly 102 is omitted from lower subassembly 104.

Figure 3:
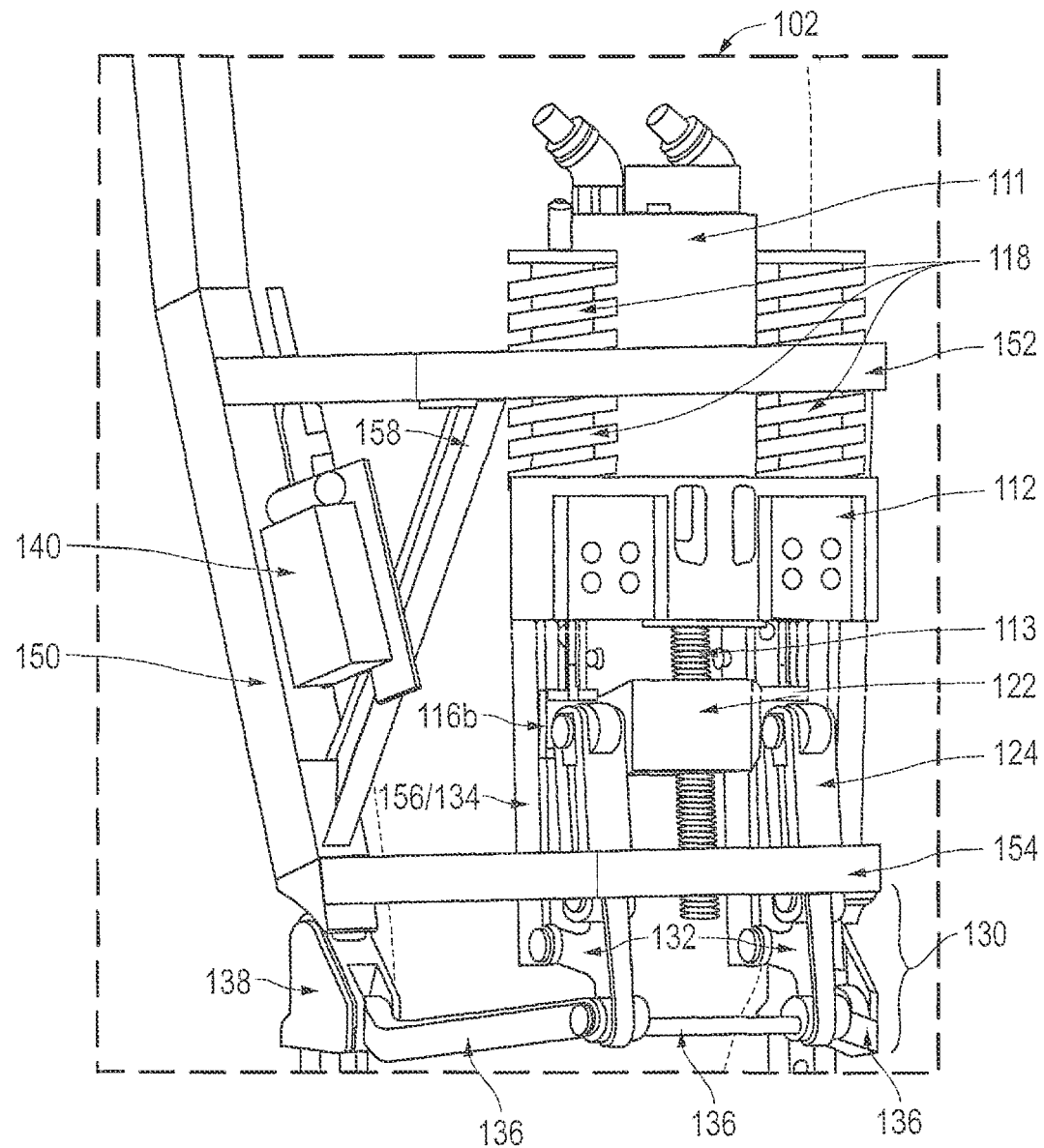
FIG. 3 is a magnified, front perspective view of the upper subassembly of the exoskeleton device shown in FIG. 1 depicting various components used to control rotation at the knee joint of the exoskeleton device.
Figure 5:
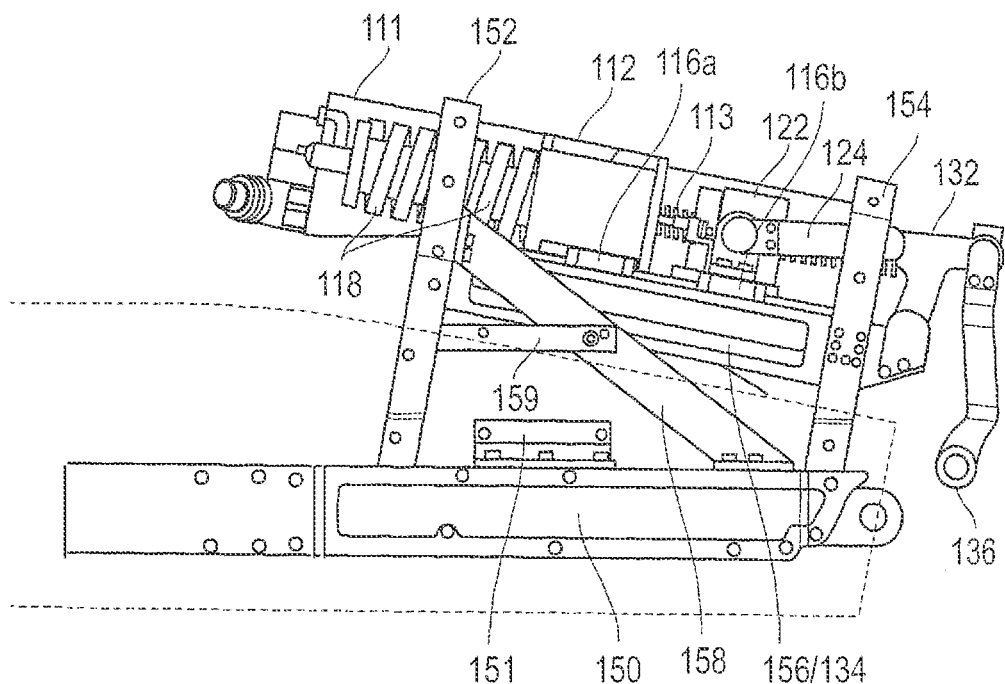
FIG. 5 is a side view of the upper subassembly of the exoskeleton device shown in FIG. 1 depicting various components used to control rotation at the knee joint of the exoskeleton device.

The upper subassembly 102 and lower subassembly 104 of the exoskeleton device 100 may further include a plurality of structural elements that provide structural support for the exoskeleton. For example, the upper and lower subassembly may each include a first structural element 150 that extends longitudinally along the outside of the wearer's upper and lower leg, respectively. In some embodiments, the control circuitry 140 used to control actuation of the SEA 110 and articulation of the knee and ankle joints may be mounted onto the first structural element 150, as shown in FIGS. 1-3. In some embodiments, a mounting bracket 151 may be fixedly attached to the first structural element 150 for mounting at least a portion of the control circuitry 140 thereto, as shown in FIG. 5.

The upper and lower subassembly may also include a second structural element 152 and a third structural element 154 that arch laterally across the wearer's upper and lower leg. A lower portion of the second and third structural elements 152, 154 is fixedly attached to the first structural element 150. An upper portion of the second and third structural elements 152, 154 arches up and around to the inside of the wearer's leg. A fourth set of structural elements 156 is attached between the second and third structural elements 152, 154. As described in more detail below, a first pair of linear guide mechanisms 116a and a second pair of linear guide mechanisms 116b may be attached to the fourth set of structural elements 156 for supporting the SEA 110 and slider-crank mechanism 120. In some embodiments, a fifth structural element 158 may be coupled between the first structural element 150 and the second structural element 152, and a sixth structural element 159 may be coupled between fifth structural element 158 and the second structural element 152 to enhance structural integrity of the exoskeleton 100, as shown in FIG. 5.

Figure 4:
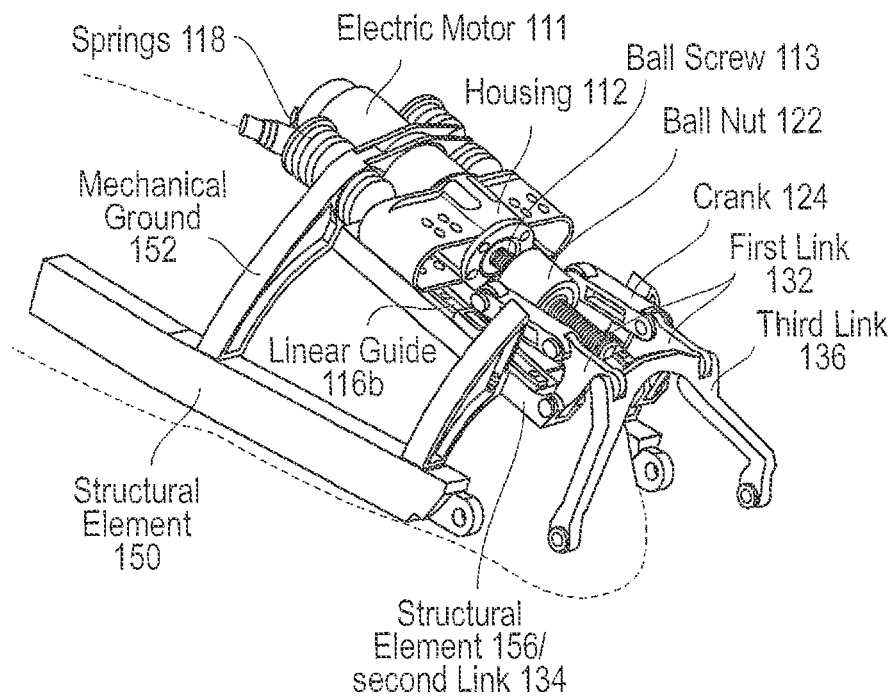
FIG. 4 is a side perspective view of the upper subassembly of the exoskeleton device shown in FIG. 1 depicting various components used to control rotation at the knee joint of the exoskeleton device.

As noted above, SEAs generally contain a motor to generate mechanical power, a speed reduction mechanism to amplify motor torque, an elastic component to sense force, and a transmission mechanism to route mechanical power to the output joint. In the SEA 110 shown in FIGS. 1-5, an electric motor 111 mounted directly to actuator housing 112 is used to convert electrical voltage and current into mechanical velocity and torque. As shown in FIGS. 3-5, one end of electric motor 111 is mounted within a central portion of actuator housing 112. In some embodiments, the central portion of actuator housing 112 may be shaped and dimensioned to accommodate electric motor 111. In the illustrated embodiment shown in FIGS. 1-5, for example, electric motor 111 includes a substantially cylindrical shaped housing. In such an embodiment, the central portion of actuator housing 112 may also comprise a cylindrical shape and may be sized, so that the end of electric motor 111 fits snuggly within the central portion.

In some embodiments, electric motor 111 may be a liquid cooled, brushless DC motor. One example of a liquid cooled, brushless DC motor, which was developed by the present inventors, is described in US Patent Application Publication No. 2017/03412287, entitled "Viscoelastic Liquid-Cooled Actuator," and incorporated herein in its entirety. However, it is expressly noted that electric motor 111 is not strictly limited to liquid cooled, brushless DC motors and may be alternatively implemented with other types of electric motors, which are suitable for exoskeletons.

Electric motor 111 converts the current received from control circuitry 140 into mechanical velocity and torque, which is transferred directly to ball screw 113. Although not shown clearly in the drawings, ball screw 113 is coupled to a shaft of electric motor 111 via a shaft coupler (not shown) included within actuator housing 112. As the motor shaft rotates, the shaft coupler transfers rotational motion of the shaft directly to the ball screw. Ball screw 113 provides a speed reduction mechanism to amplify motor torque and efficiently converts rotational motion of the ball screw into linear motion at the input of slider-crank mechanism 120.

The elastic component of SEA 110 is implemented with two pairs of preloaded springs 118 (four springs total), which are positioned alongside the electric motor 111 and coupled to the mechanical ground of the actuator. In the illustrated embodiment, the second structural element 152 is either coupled to the mechanical ground, or functions as the mechanical ground of the actuator. The lower spring in each pair of springs 118 is coupled to the actuator housing 112. More specifically, the lower spring in each pair of springs 118 is coupled to a respective side portion of actuator housing 112, as shown in FIGS. 3 and 4.

As noted above, a first pair of linear guide mechanisms 116a is attached to the fourth set of structural elements 156 for supporting SEA 110. Each linear guide mechanism 116a includes a rail portion and a guide portion, which is coupled to and configured to slide along the rail portion. As shown in FIG. 5, the rail portions of the linear guide mechanisms 116a are fixedly attached (e.g., via screws) to the fourth set of structural elements 156, and the guide portions of the linear guide mechanisms 116a are fixedly attached (e.g., via screws) to a lower surface of the side portions of the actuator housing 112. The first pair of linear guide mechanisms 116a accommodates spring deflection by allowing SEA 110 to slide up and down the fourth set of structural elements 156 as the plurality of springs 118 expand and contract.

Spring deflection is detected by a spring deflection sensor (not shown) arranged within actuator housing 112. Although not limited to such, the spring deflection sensor may comprise a Novotechnik VertX sensor, in one embodiment. The spring deflection sensor measures deflection of the springs 118 as ball screw 113 is rotated under the control of electric motor 111. The spring deflection sensor generates a signal, based on the deflection of the springs 118, that indicates the amount of force exerted by the actuator. Although beyond the scope of the present disclosure, this signal may be transmitted to the controller circuitry 140 coupled to electric motor 111 to create an active feedback force control loop for controlling the motor. In general, SEA 110 may be controlled using any standard feedback control technique, one of which is described in N. Paine, J. Mehling, J. Holley, N. Radford, G. Johnson, C. Fok and L. Sentis, entitled "*Actuator Control for the NASA-JSC Valkyrie Humanoid Robot: A Decoupled Dynamics Approach for Torque Control of Series Elastic Robots*," herein incorporated by reference in its entirety.

Slider-crank mechanism 120 includes a ball nut 122 and two crank portions 124. The ball nut 122 is arranged between crank portions 124 and is coupled (on lateral sides of the ball nut) to upper ends of each crank portion 124. Ball nut 122, which is concentrically arranged around ball screw 113, is configured to convert rotational motion of ball screw 113 into linear motion of ball nut 122 to drive the crank portions 124. In other words, ball nut 122 acts as the "slider" portion of slider-crank mechanism 120. As ball screw 113 rotates, ball nut 122 slides up and down the ball screw depending on the direction of rotation. The crank portions 124 of the slider-crank mechanism 120 convert the linear motion of ball nut 122 back into rotational motion at the lower ends of crank portions 124 (i.e., at the output of the slider-crank mechanism 120).

As noted above, a second pair of linear guide mechanisms 116b is attached to the fourth set of structural elements 156 for supporting slider-crank mechanism 120. Each linear guide mechanism 116b includes a rail portion and a guide portion, which is coupled to and configured to slide along the rail portion. As shown in FIGS. 3-5, the rail portions of linear guide mechanisms 116b are fixedly attached (e.g., via screws) to the fourth set of structural elements 156, and the guide portions of the linear guide mechanisms 116b are fixedly attached (e.g., via screws) to an upper end of the crank portions 124 of slider-crank mechanism 120. The guide portions slide along the rail portions of linear guide mechanisms 116b as ball nut 122 slides up and down ball screw 113. In this manner, the second pair of linear guide mechanisms 116b provides structural stability to the slider-crank mechanism 120, and allows ball nut 122 and crank portions 124 to slide in a linear motion as the ball screw 113 rotates.

The crank portions 124 of slider-crank mechanism 120 act as inputs to a pair of four-bar linkage mechanisms 130, which translate the mechanical energy of the crank into the appropriate motion profile for use with the knee joint of the exoskeleton. Each four-bar linkage mechanism 130 may include a first link 132, a second link 134, a third link 136 and a fourth link 138. The first link 132 included within each four-bar linkage mechanism 130 is a T-shaped link having a first end rotationally coupled to a lower end of one of the crank portions 124, a second end rotationally coupled to the second link 134, and a third end rotationally coupled to the third link 136. In the embodiment shown in FIGS. 3-5, the fourth set of structural elements 156 used to support the SEA 110 and slider-crank mechanism 120 may also be used as the second link 134 in the four-bar linkage mechanisms 130.

As shown in FIGS. 3-5, the third link 136 is shared between the pair of four-bar mechanisms 130. The shared third link 136 extends in a lateral direction across the wearer's knee joint to rotationally couple with the third ends of the T-shaped first links 132 included within the pair of four bar linkage mechanisms 130. The shared third link 136 further extends in the dorsal direction to rotationally couple with the fourth links 138, which are positioned on either side of the wearer's knee joint. The fourth link 138 is coupled to the first structural element 150 of the upper subassembly 102. In this manner, the individual links of the four-bar linkage mechanism 130 work together to provide a complex motion profile that emulates the kinematics of the knee joint.

One property of mechanical linkages is that the relationship between the input of the linkage and the output of the linkage is typically non-linear and angle-dependent. The linkages used in exoskeleton 100 create an angle-dependent "advantage" from the SEA 110 to the rotary (knee or ankle) joint. During development of exoskeleton 100, the present inventors analyzed the performance requirements of each joint for a variety of tasks and identified angles of human knees and ankles that require more torque or more speed. Based on the analysis, the present inventors changed the parameters of each linkage of the four-bar linkage mechanism 130 to best match the performance metrics obtained from human behavior. This is something that can't be done with simpler rotary actuator-based exoskeletons.

Figure 6:
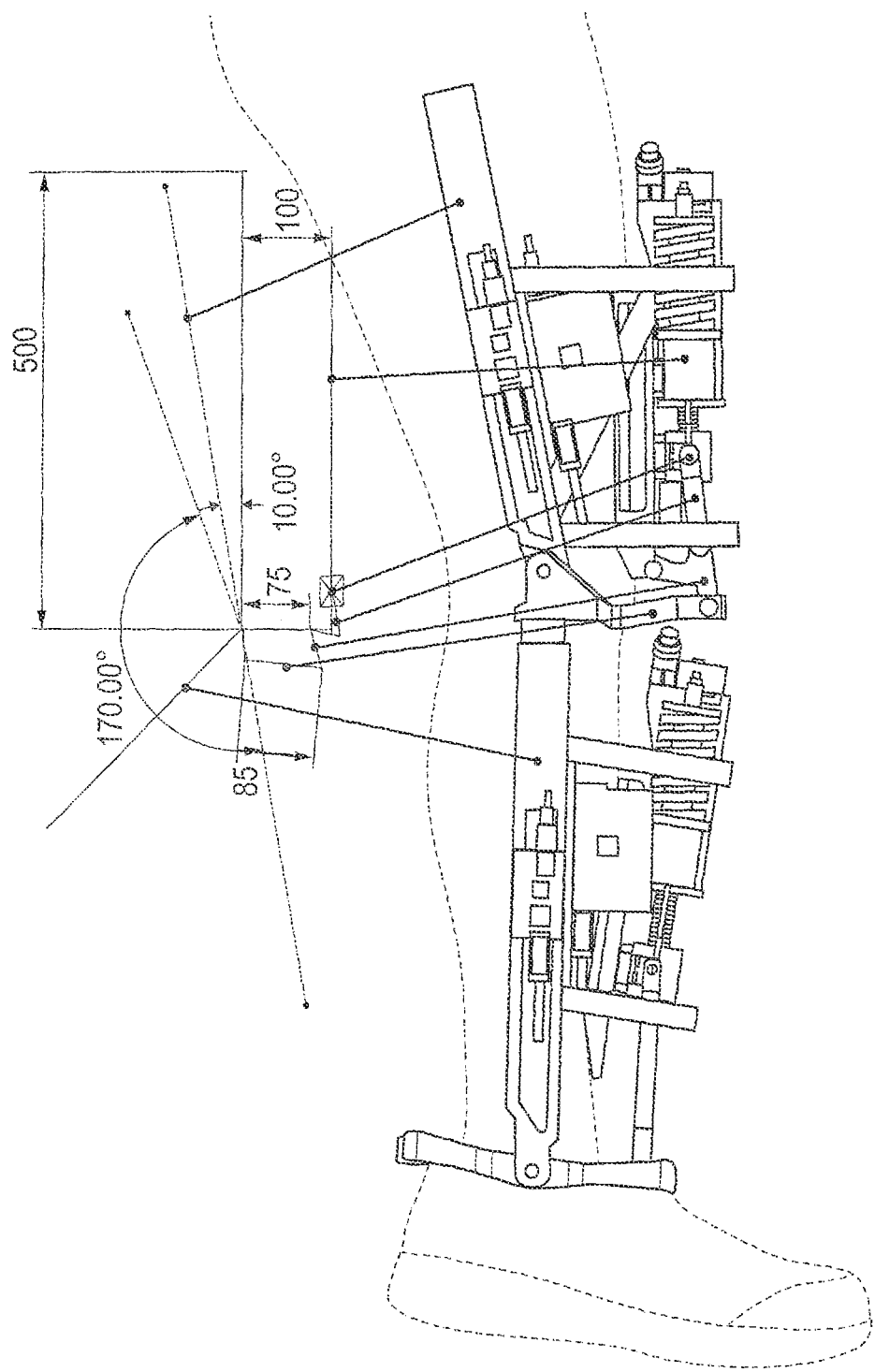
FIG. 6 is a side view of the exoskeleton device shown in FIG. 1, and includes a diagram illustrating kinematics of the linkage used in the knee joint of the exoskeleton device.
Figure 7:
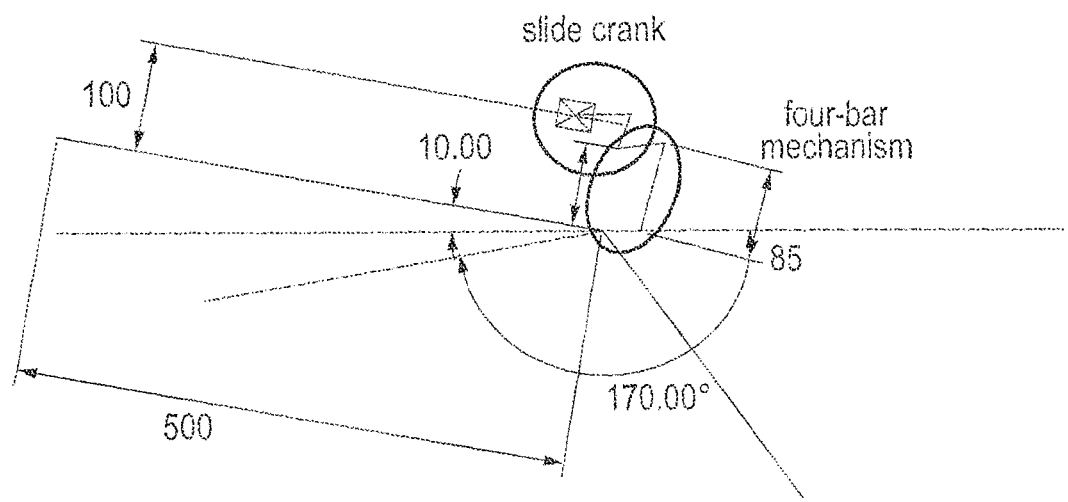
FIG. 7 is a diagram illustrating the exoskeleton knee linkage fully extended.
Figure 8:
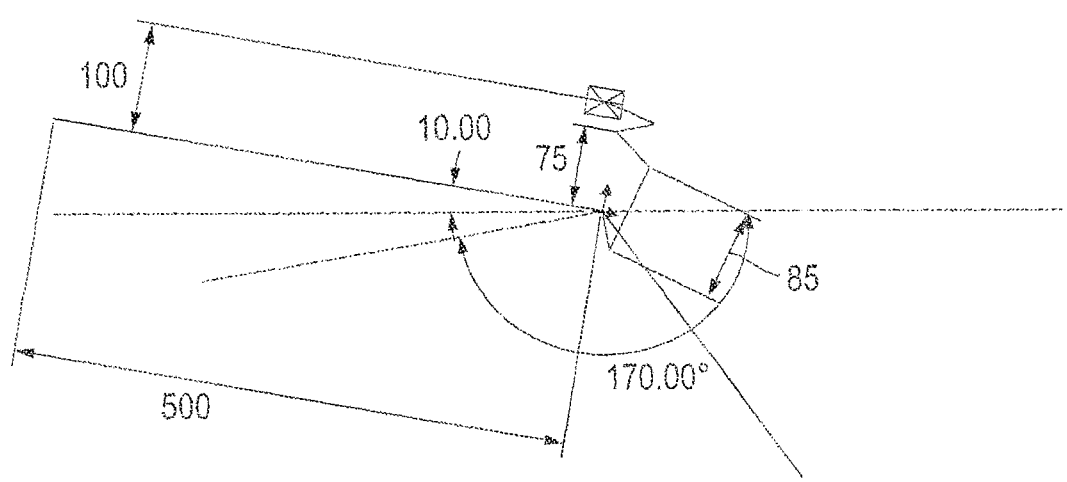
FIG. 8 is a diagram illustrating the exoskeleton knee linkage fully contracted.

FIGS. 6-8 depict the kinematics of the linkage used in the knee joint of exoskeleton 100. More specifically, FIGS. 6 and 7 illustrate the kinematics when the exoskeleton knee linkage is fully extended, while FIG. 8 depicts the kinematics when the exoskeleton knee linkage is fully contracted.

The actuation system utilized by the exoskeleton device 100 shown in FIGS. 1-5 is unique, compared to other exoskeleton designs, in that it is powerful, efficient, low-profile and lightweight. More specifically, the combination of SEA 110, slider-crank mechanism 120 and four-bar linkage mechanism 130 greatly reduces the weight and bulk of the actuation system used in exoskeleton device 100, compared to actuation systems used in other exoskeleton devices. This makes exoskeleton device 100 particularly well-suited for performance-oriented orthotic, prosthetic and other robotic applications. One such application is shown in FIGS. 9-13.

Figure 9:
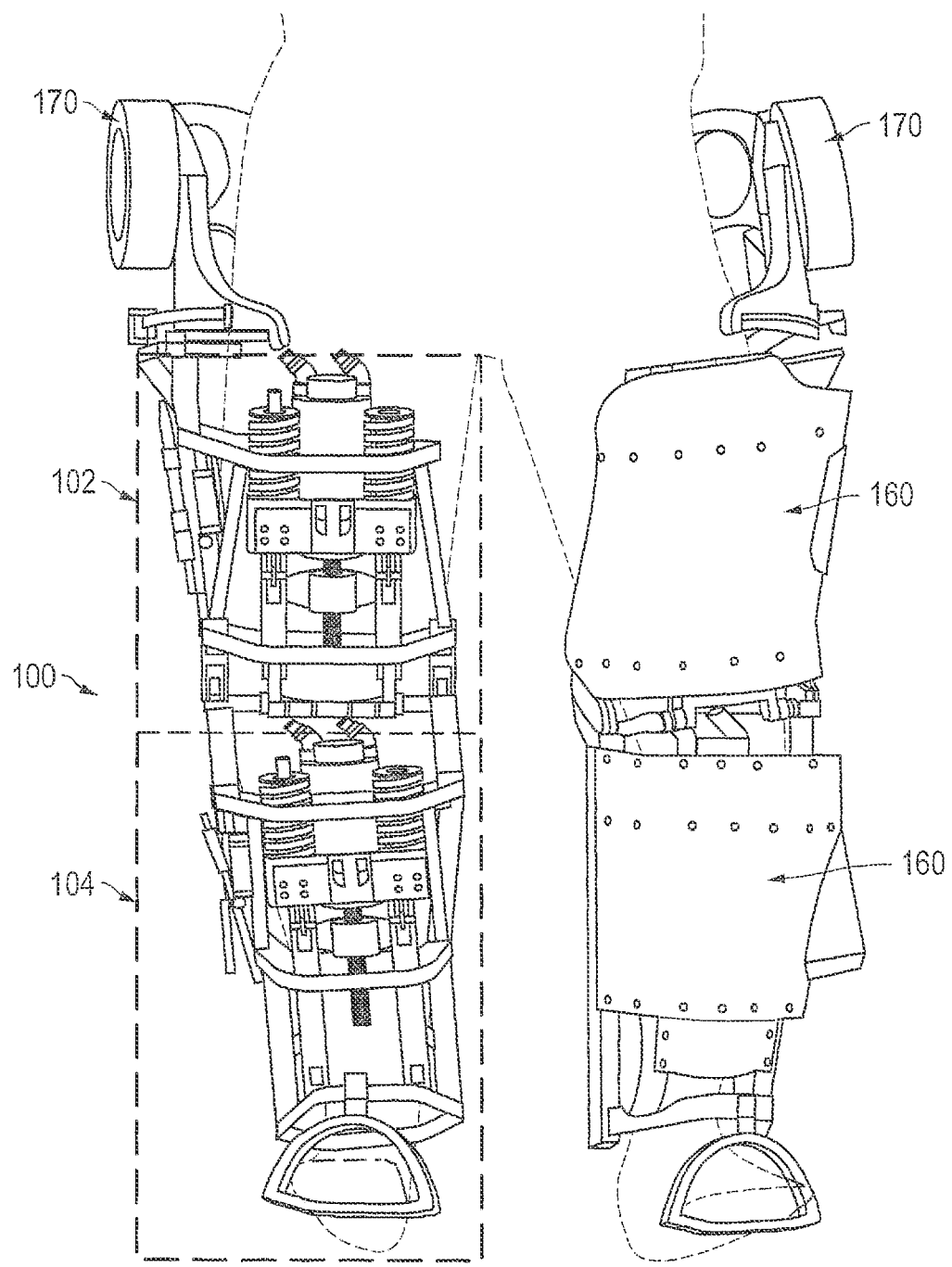
FIG. 9 is a front view of a robotic exoskeleton comprising the exoskeleton device shown in FIG. 1.
Figure 10:
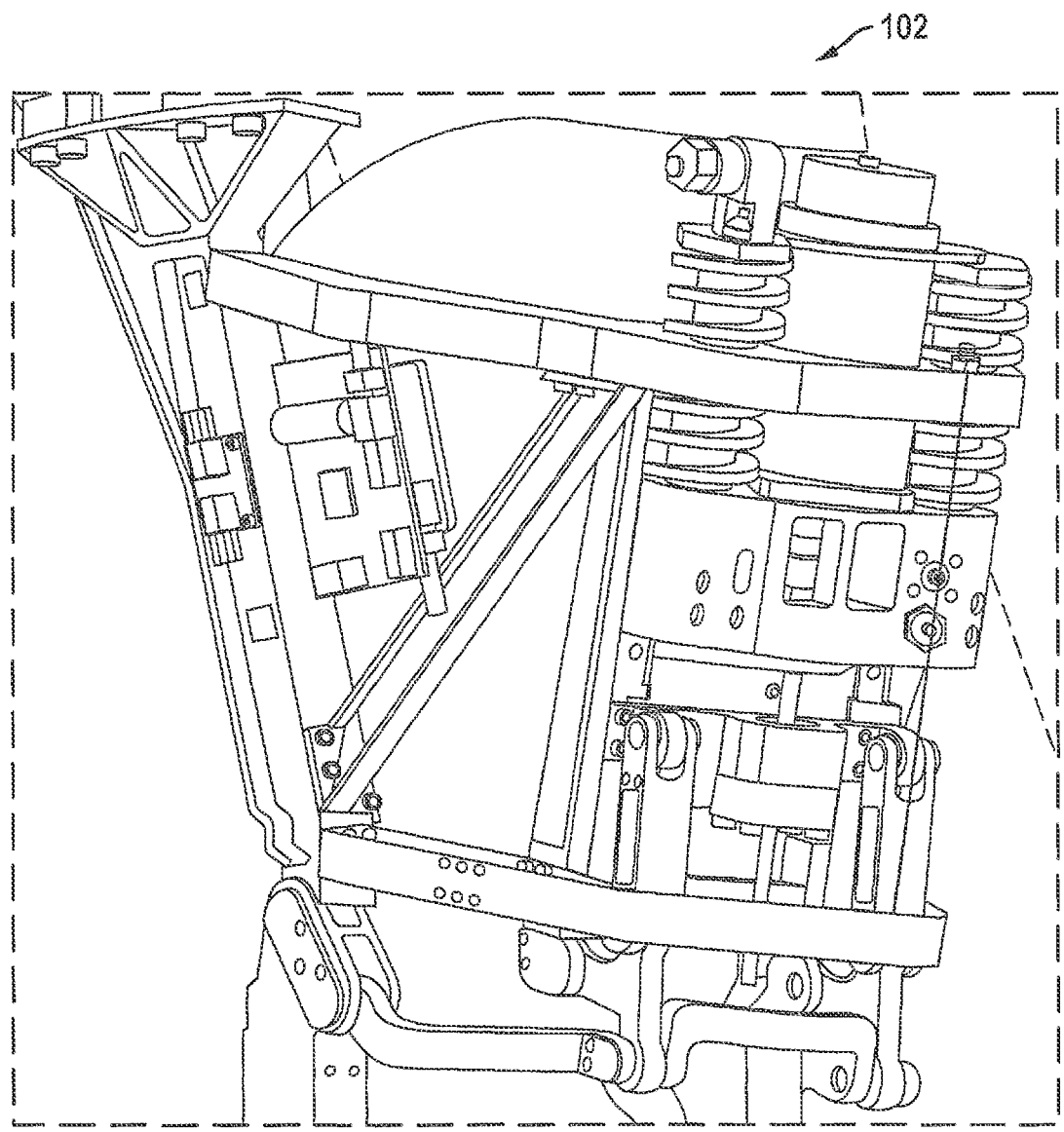
FIG. 10 is a magnified, front perspective view of the upper subassembly of the exoskeleton device shown in FIG. 9.
Figure 11:
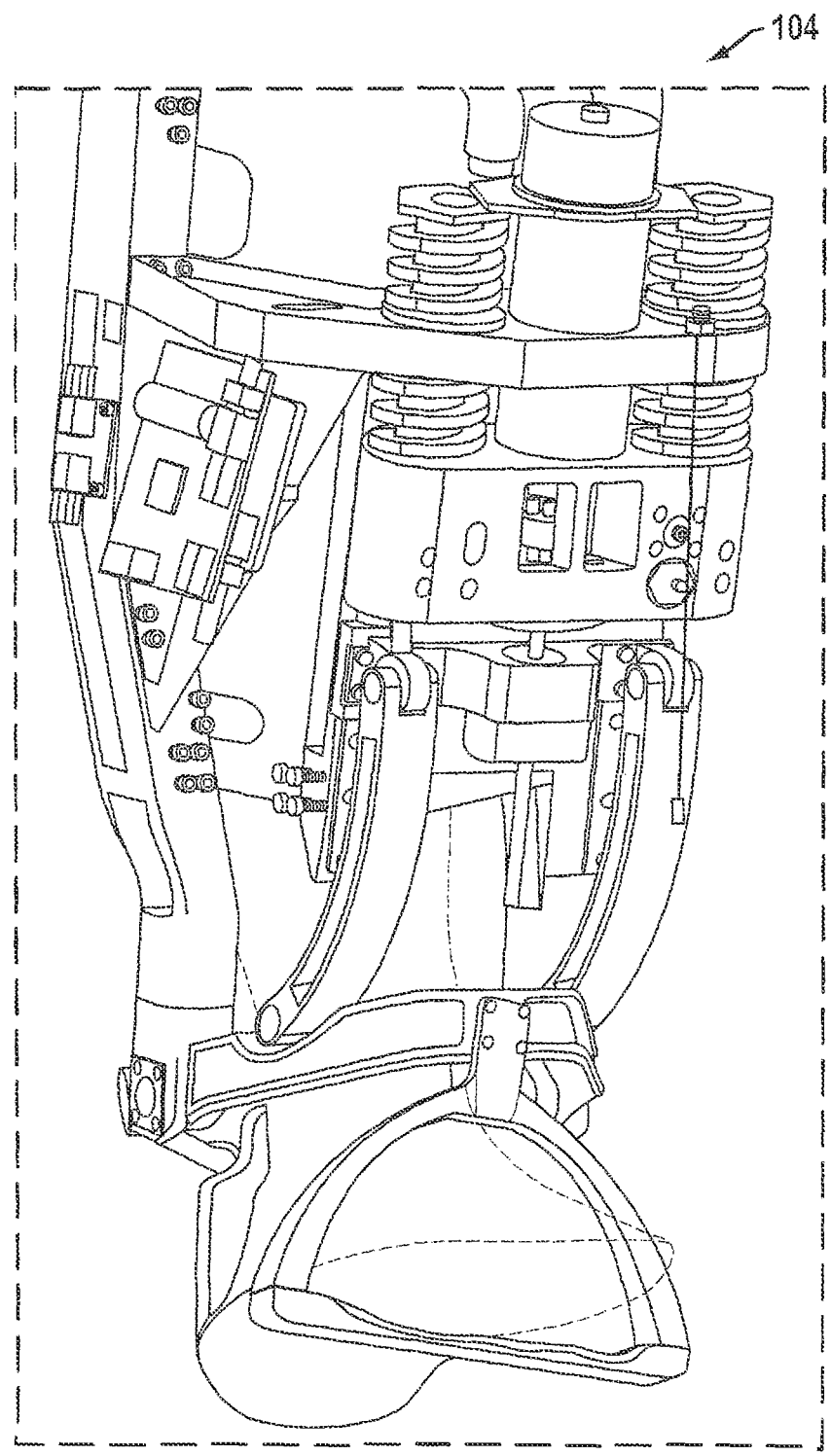
FIG. 11 is a magnified, front perspective view of the lower subassembly of the exoskeleton device shown in FIG. 9.
Figure 12:
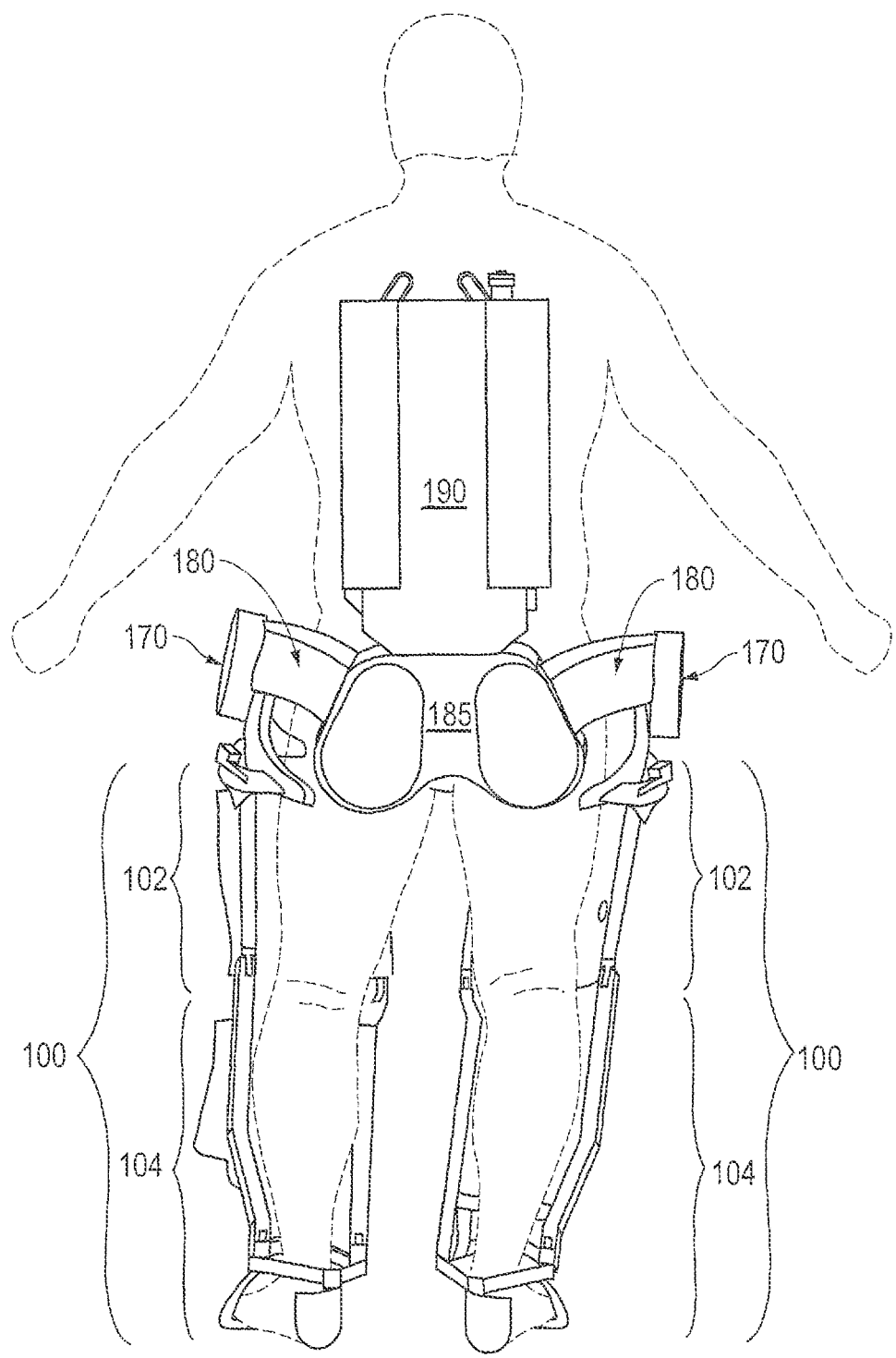
FIG. 12 is a back view of the robotic exoskeleton shown in FIG. 9.
Figure 13:
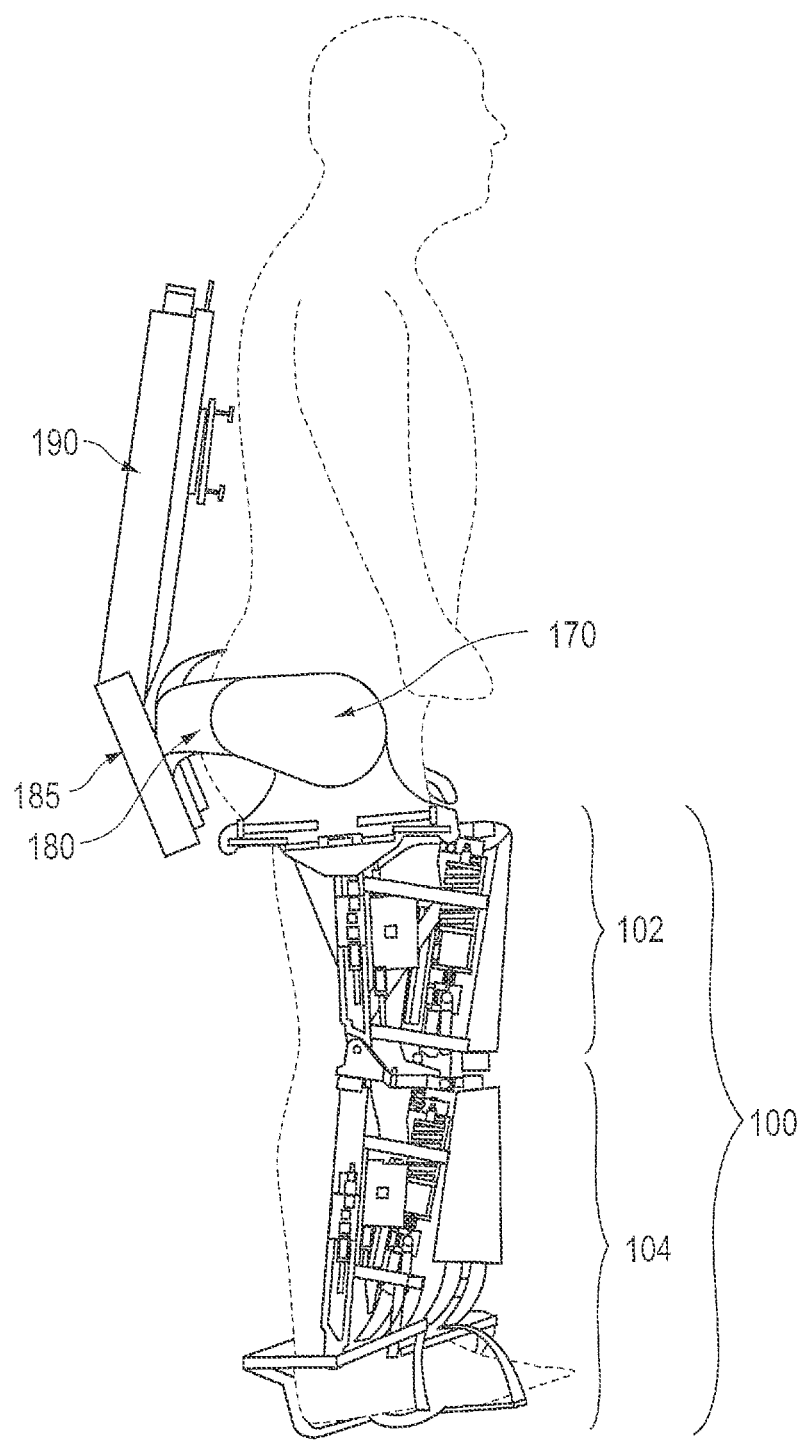
FIG. 13 is a side view of the robotic exoskeleton shown in FIG. 9.

FIGS. 9-13 depict various views of a lower extremity robotic exoskeleton comprising the exoskeleton device 100 shown in FIG. 1. More specifically, FIG. 9 provides a front view, FIG. 12 provides a back view and FIG. 13 provides a side view of a robotic exoskeleton comprising the exoskeleton device 100 shown in FIG. 1. As noted above, exoskeleton device 100 may generally include an upper subassembly 102 for applying assistive torques to the wearer's knee joint and a lower subassembly 104 for applying assistive torques to the wearer's ankle joint. FIGS. 10 and 11 provide magnified, front perspective views of the upper subassembly 102 and lower subassembly 104 included within FIG. 9. The upper and lower subassemblies shown in FIGS. 9-11 may be generally configured as described above with respect to FIGS. 1-5.

In some embodiments, an upper subassembly 102 and a lower subassembly 104 may be fitted to each of the wearer's legs to apply assistive torques to the knee and ankle joints of both legs, as shown in FIG. 9. In other embodiments, an upper subassembly 102 and lower subassembly 104 may be fitted to only one of the wearer's legs, as implicated in FIGS. 1 and 2. In some embodiments, a protective covering 160 may be attached to the upper and lower subassemblies to protect the components contained therein. In other embodiments, the protective covering may be considered to an aesthetic feature, which may or may not be omitted from the design.

As shown in FIGS. 9, 12 and 13, the upper subassembly 102 of each exoskeleton device 100 is attached to a hip joint assembly 170 positioned on either side of the wearer's hips. Each hip joint assembly 170 may generally include a rotary actuator to control flexion/extension of the hip joint. Like the linear actuators used in the knee and ankle joints, the rotary actuators used in the hips may be implemented as series elastic actuators (SEAs). One unique aspect of the robotic exoskeleton shown in FIGS. 9-13 is that all actuators used in the design are series elastic actuators, which enables torque to be precisely controlled at the hip, knee and ankle joints. This high fidelity torque control is helpful for interfacing with a human (from both a safety and control performance standpoint). SEAs also provide the added benefit of robustness to impacts.

A curved hollow structure 180 is coupled to the hip joint assemblies 170 on either side of the wearer's hips to provide a load path from the power unit 190 to ground. A rotary actuator 185 attached to the curved hollow structure 180 provides actuation for the hip abduction/adduction degree of freedom. A power unit 190 is coupled to rotary actuator 185 to provide power to the electronic components (e.g., SEA 110, control circuitry 140 and rotary actuator 185) of the exoskeleton device 100. In some embodiments, power unit 190 may also include supply equipment for a liquid cooling system, which may include, for example, a pump, reservoir, and heat exchanger (radiator). In some embodiments, the liquid cooling system may be coupled to the SEAs in the knee and ankle joints; the rotary actuators used in the hip may be passively cooled.

While the invention may be adaptable to various modifications and alternative forms, specific embodiments have been shown by way of example and described herein. However, it should be understood that the invention is not intended to be limited to the particular forms disclosed. Rather, the invention is to cover all modifications, equivalents, and alternatives falling within the spirit and scope of the invention as defined by the appended claims. Moreover, the different aspects of the disclosed systems and methods may be utilized in various combinations and/or independently. Thus, the invention is not limited to only those combinations shown herein, but rather may include other combinations.

What is claimed is:

1. An exoskeleton device, comprising:
   a series elastic actuator (SEA) comprising:
      a motor; and
      a ball screw coupled to a shaft of the motor via a shaft coupler, which transfers rotational motion of the shaft directly to the ball screw;
   a slider-crank mechanism comprising a ball nut and a crank, wherein the ball nut is configured to convert rotational motion of the ball screw into linear motion of the ball nut to drive the crank; and
   a pair of four-bar linkage mechanisms coupled to an output of the crank and configured to provide a complex motion profile that emulates kinematics of a wearer's joint each four-bar linkage mechanism including a first link, a second link, and a fourth link, and a third link shared between the pair of four bar linkage mechanisms.

2. The exoskeleton device as recited in claim 1, wherein the SEA further comprises:

two pairs of springs, wherein each pair of springs is positioned alongside a different side of the motor; and
an actuator housing, wherein the motor and a lower spring in each pair of springs are coupled to the actuator housing.

3. The exoskeleton device as recited in claim 2, further comprising a first linear guide mechanism attached to a structural element of the exoskeleton device to provide structural support to, and allow linear motion of, the SEA.

4. The exoskeleton device as recited in claim 3, wherein the first linear guide mechanism comprises a rail portion and a guide portion, which is coupled to and configured to slide along the rail portion, and wherein the rail portion is attached to the structural element of the exoskeleton device and the guide portion is attached to a lower surface of the actuator housing.

5. The exoskeleton device as recited in claim 3, wherein an upper end of the crank is coupled to the ball nut and a lower end of the crank is coupled to an input of a first four-bar linkage mechanism of the pair of four-bar linkage mechanisms, and wherein the crank converts the linear motion of the ball nut back into rotational motion at the input of the first four-bar linkage mechanism.

6. The exoskeleton device as recited in claim 5, further comprising a second linear guide mechanism attached to the structural element of the exoskeleton device, wherein the second linear guide mechanism provides structural support to, and allows linear motion of, the ball nut and crank.

7. The exoskeleton device as recited in claim 6, wherein the second linear guide mechanism comprises a rail portion and a guide portion, which is coupled to and configured to slide along the rail portion, and wherein the rail portion is attached to the structural element of the exoskeleton device and the guide portion is attached to the upper end of the crank.

8. The exoskeleton device as recited in claim 6, wherein:
the first link of at least one four-bar linkage mechanism of the pair of four-bar linkage mechanisms is a T-shaped link having a first end rotationally coupled to the upper end of the crank, a second end rotationally coupled to the second link, and a third end rotationally coupled to the third link;
the third link extends in a dorsal direction to rotationally couple with the fourth link of each four-bar linkage mechanism of the pair of four-bar linkage mechanisms; and
the fourth link of each four-bar linkage mechanism of the pair of four-bar linkage mechanisms is positioned on a respective side of the wearer's joint.

9. The exoskeleton device as recited in claim 8, wherein the second link of at least one four-bar linkage mechanism of the pair of four-bar linkage mechanisms is the structural element of the exoskeleton device to which the first linear guide mechanism and the second linear guide mechanism are attached.

10. The exoskeleton device as recited in claim 1, wherein the shared third link extends in a lateral direction across the wearer's knee joint to rotationally couple with the third ends of the first links included within the pair of four-bar linkage mechanisms.

11. A lower extremity robotic exoskeleton, comprising:
an upper subassembly for applying assistive torques to a wearer's knee joint, wherein the upper subassembly comprises:
a first series elastic actuator (SEA) comprising a motor and a ball screw, wherein a shaft of the motor is coupled to rotate the ball screw;
a first slider-crank mechanism comprising a ball nut and a crank, wherein the ball nut is configured to convert rotational motion of the ball screw into linear motion of the ball nut to drive the crank;
a pair of four-bar linkage mechanisms coupled to an output of the crank and configured to provide a complex motion profile that emulates kinematics of a wearer's joint each four-bar linkage mechanism including a first link, a second link, and a fourth link, wherein a third link is shared between the pair of four-bar linkage mechanisms; and
control circuitry that uses a force detected by the first SEA to control rotation at the wearer's knee joint.

12. The lower extremity robotic exoskeleton as recited in claim 11, wherein the first link of each four-bar linkage mechanism of the pair is a T-shaped link having a first end rotationally coupled to an upper end of the crank, a second end rotationally coupled to the second link, and a third end rotationally coupled to the shared third link.

13. The lower extremity robotic exoskeleton as recited in claim 12, wherein the shared third link extends in a dorsal direction to rotationally couple with the fourth link of each four-bar linkage mechanism of the pair, the fourth link of each four-bar linkage mechanism of the pair being positioned on a respective side of the wearer's knee joint, and wherein the shared third link further extends in a lateral direction across the wearer's knee joint to rotationally couple with the third ends of the first links included within the pair of four-bar linkage mechanisms.

14. The lower extremity robotic exoskeleton as recited in claim 11, further comprising a lower subassembly for applying assistive torques to the wearer's ankle joint, wherein the lower subassembly comprises:
a second series elastic actuator (SEA) comprising a motor and a ball screw, wherein a shaft of the motor is coupled to rotate the ball screw;
a second slider-crank mechanism comprising a ball nut and a crank, wherein the ball nut is configured to convert rotational motion of the ball screw into linear motion of the ball nut to drive the crank; and
control circuitry that uses a force detected by the second SEA to control rotation at the wearer's ankle joint.

15. The lower extremity robotic exoskeleton as recited in claim 14, wherein the first SEA and the second SEA each comprise:
an actuator housing;
two pairs of springs, wherein each pair of springs is positioned along a different side the motor, and wherein a lower spring in each pair of springs is coupled to the actuator housing; and
a spring deflection sensor arranged within the actuator housing for detecting the force exerted by the SEA as the springs compress and expand.

16. The lower extremity robotic exoskeleton as recited in claim 15, wherein the upper subassembly and the lower subassembly each further comprise a plurality of structural elements that provide structural support for the exoskeleton, wherein the plurality of structural elements include:
a first structural element that extends longitudinally along an outside of the wearer's leg;
a second structural element and a third structural element that arch laterally across the wearer's leg, wherein lower portions of the second and third structural elements are fixedly attached to the first structural element; and
a fourth set of structural elements, which are coupled between the second and third structural elements and configured to support the first SEA and the second SEA and the first slider-crank mechanism and the second slider-crank mechanism.

17. The lower extremity robotic exoskeleton as recited in claim 16, wherein the upper subassembly and the lower subassembly each further comprise:
   a first linear guide mechanism coupled between the fourth set of structural elements and the actuator housing, wherein the first linear guide mechanism enables the actuator housing of the first SEA and the actuator housing of the second SEA to slide up and down the fourth set of structural elements with compression and expansion of the springs; and
   a second linear guide mechanism coupled between the fourth set of structural elements and an upper end of the crank, wherein the second linear guide mechanism enables the ball nut and the crank to slide in a linear motion as the ball screw rotates.

18. The lower extremity robotic exoskeleton as recited in claim 14, wherein the upper subassembly and the lower subassembly are fitted to one of the wearer's legs.

19. The lower extremity robotic exoskeleton as recited in claim 18, further comprising a second upper subassembly and a second lower subassembly fitted to another one of the wearer's legs, wherein the second upper subassembly is identical to the upper subassembly, and wherein the second lower subassembly is identical to the lower subassembly.

20. The lower extremity robotic exoskeleton as recited in claim 19, further comprising a pair of hip joint assemblies, each positioned on either side of the wearer's hips, wherein the pair of hip joint assemblies is coupled to the upper subassembly and the second upper subassembly and configured to control flexion/extension of the wearer's hip joint.

21. The lower extremity robotic exoskeleton as recited in claim 20, further comprising:
   a curved hollow structure coupled to the pair of hip joint assemblies;
   a rotary actuator coupled to the curved hollow structure and configured to provide abduction/adduction actuation for the wearer's hip joint; and
   a power unit coupled to the rotary actuator and configured to provide power to the rotary actuator, as well as to the first SEA, the second SEA, and the control circuitry included within the upper subassembly, the lower subassembly, the second upper subassembly and the second lower subassembly.

22. An exoskeleton device, comprising:
   a series elastic actuator (SEA) comprising:
      a motor;
      a ball screw coupled to a shaft of the motor via a shaft coupler, which transfers rotational motion of the shaft directly to the ball screw;
      two pairs of springs, wherein each pair of springs is positioned alongside a different side of the motor; and
      an actuator housing, wherein the motor and a lower spring in each pair of springs are coupled to the actuator housing;
   a slider-crank mechanism comprising a ball nut and a crank, wherein the ball nut is configured to convert rotational motion of the ball screw into linear motion of the ball nut to drive the crank;
   a first linear guide mechanism attached to a structural element of the exoskeleton device to provide structural support to, and allow linear motion of, the SEA;
   a second linear guide mechanism attached to the structural element of the exoskeleton device, wherein the second linear guide mechanism provides structural support to, and allows linear motion of, the ball nut and crank; and
   a four-bar linkage mechanism coupled to an output of the crank and configured to provide a complex motion profile that emulates kinematics of a wearer's joint,
   wherein:
      an upper end of the crank is coupled to the ball nut and a lower end of the crank is coupled to an input of the four-bar linkage mechanism, and wherein the crank converts the linear motion of the ball nut back into rotational motion at the input of the four-bar linkage mechanism;
      the four bar linkage mechanism comprises a first link, a second link, a third link and a fourth link:
      the first link is a T-shaped link having a first end rotationally coupled to the upper end of the crank, a second end rotationally coupled to the second link, and a third end rotationally coupled to the third link;
      the third link extends in a dorsal direction to rotationally couple with the fourth link, which is positioned on one side of the wearer's joint.

23. The exoskeleton device as recited in claim 22, wherein the first linear guide mechanism comprises a rail portion and a guide portion, which is coupled to and configured to slide along the rail portion, and wherein the rail portion is attached to the structural element of the exoskeleton device and the guide portion is attached to a lower surface of the actuator housing.

24. The exoskeleton device as recited in claim 22, wherein the second linear guide mechanism comprises a rail portion and a guide portion, which is coupled to and configured to slide along the rail portion, and wherein the rail portion is attached to the structural element of the exoskeleton device and the guide portion is attached to the upper end of the crank.

25. The exoskeleton device as recited in claim 22, wherein the second link is the structural element of the exoskeleton device to which the first linear guide mechanism and the second linear guide mechanism are attached.

26. The exoskeleton device as recited in claim 22, wherein the third link extends in a lateral direction across the wearer's knee joint.

\* \* \* \* \*

UNITED STATES PATENT AND TRADEMARK OFFICE
CERTIFICATE OF CORRECTION

| | |
|---|---|
| PATENT NO. | : 12,036,669 B2 |
| APPLICATION NO. | : 16/979057 |
| DATED | : July 16, 2024 |
| INVENTOR(S) | : Nicholas Arden Paine and Jonas Fox |

It is certified that error appears in the above-identified patent and that said Letters Patent is hereby corrected as shown below:

On the Title Page

Page 2, Column 2, (Item (56) Other Publications), Line 26, delete "Knee-Foot Robot for Galt" and insert -- Knee-Ankle-Foot Robot for Gait --.

In the Specification

Column 3, Line 38, delete "side" and insert -- side of --.

In the Claims

Column 10, Line 62, in Claim 1, delete "joint" and insert -- joint, --.

Column 12, Line 8, in Claim 11, delete "joint" and insert -- joint, --.

Column 12, Line 48, in Claim 15, delete "side" and insert -- side of --.

Signed and Sealed this
Nineteenth Day of November, 2024

Katherine Kelly Vidal
*Director of the United States Patent and Trademark Office*